United States Patent [19]
Rohrle et al.

[11] 3,974,381
[45] Aug. 10, 1976

[54] METHOD OF ELECTRON BEAM WELDING WITH X-RAY DETECTION

[75] Inventors: Manfred Röhrle, Nellingen; Hagen Hummel, Obersulm-Weiler, both of Germany

[73] Assignee: Mahle GmbH, Stuttgart, Germany

[22] Filed: Oct. 21, 1974

[21] Appl. No.: 516,402

[30] Foreign Application Priority Data
Oct. 31, 1973 Germany............................ 2354509

[52] U.S. Cl. .................... 250/310; 219/121 EB; 250/306; 250/358 R; 250/399; 250/492 B
[51] Int. Cl.² ..................... G01M 23/00; B23K 9/00
[58] Field of Search ........... 250/358, 310, 492, 272, 250/306, 399; 219/121 EB

[56] References Cited
UNITED STATES PATENTS

| | | |
|---|---|---|
| 1,624,443 | 4/1927 | St. John.............................. 250/320 |
| 3,146,347 | 8/1967 | Ziegler............................... 250/310 |
| 3,435,211 | 3/1969 | Softky................................. 250/310 |
| 3,597,577 | 8/1973 | Guittet et al........................ 250/358 |

*Primary Examiner*—Harold A. Dixon
*Attorney, Agent, or Firm*—William A. Drucker

[57] ABSTRACT

Welding method and apparatus for detecting the penetration depth of an electron beam weld, in which X-rays which occur are guided through several plates of an absorption device to a ray receiver, the plates comprising of plurality of bores of equal diameter, which are arranged in their position to one another in such a way that the center lines of corresponding bores on the same level are in exact alignment and that the ray receiver, absorption device and workpiece are aligned in parallel with one another and are co-ordinated to one another in height.

2 Claims, 1 Drawing Figure

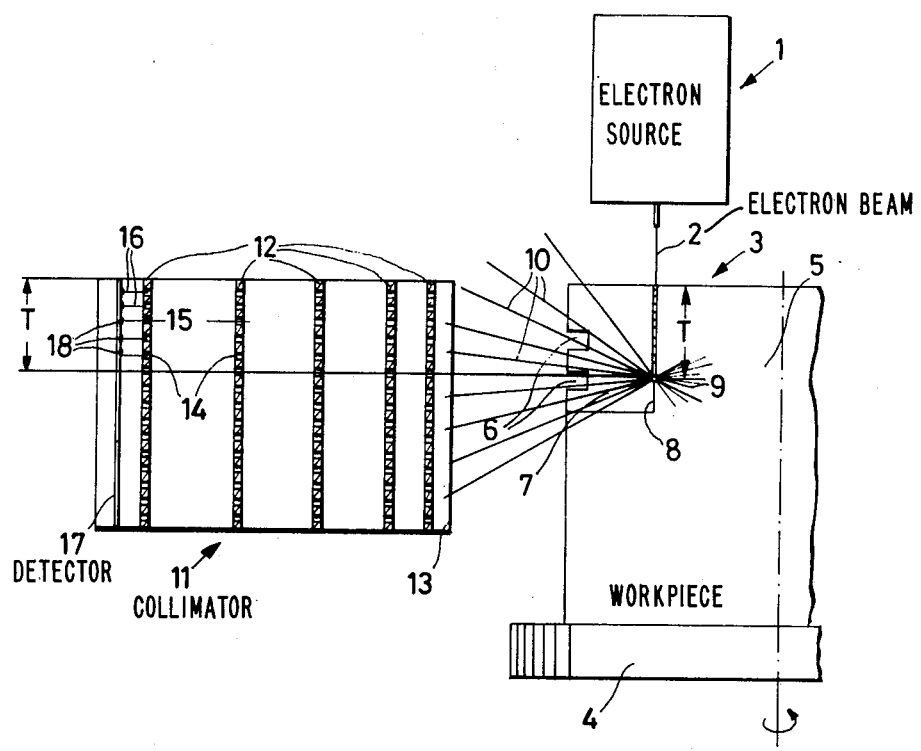

METHOD OF ELECTRON BEAM WELDING WITH X-RAY DETECTION

BACKGROUND OF THE INVENTION

1. Field of the Invention

This invention relates to a method and arrangement for measuring the weld seam depth during the electron beam welding of workpieces.

When blind seams or concealed continuous seams are welded by means of electron beams, the respective weld seam depth has to be determined in a very complicated manner. It is necessary to manufacture sample pieces from the same material and with the same dimensions as the desired workpieces. Subsequently, the desired weld seam depth is ascertained on these sample pieces in preliminary tests by cutting these sample pieces up when welding has been carried out under specified conditions.

A further impediment lies in the fact that the workpiece is heated to a considerable extent, particularly in the case of great weld seam depths, and that, as welding continues, the electron beam penetrates deeper and deeper into the workpiece. For this reason, it becomes necessary to establish, in a long series of preliminary tests, the changing welding conditions which will allow a constant weld seam depth.

When an electron beam contacts the object that is to be welded and penetrates it, there develop, at the points where the electron beam is weld effective, X-rays which expand spherically in all directions.

2. Description of the Prior Art

Such X-rays are known 'per se' and are used in German Auslegeschrift 1,299,498 for monitoring the ray impact range in instruments used for work by means of corpuscular rays. In this instance a picture of the respective surface of the ray impact region is reproduced.

SUMMARY OF THE INVENTION

The task underlying the invention is therefore to provide a method as well as an appropriate apparatus, of the kind mentioned at the beginning, for performing the method, whereby a continuous read-out of the respective weld seam depth is made possible whilst the workpiece is being welded.

According to the invention there is provided a method for determining the depth of a weld internal of a work-piece during electron beam welding, said method comprising the steps of:

i. supporting a workpiece in a workpiece support;
ii. directing an electron beam into said workpiece for effecting a weld within the workpiece;
iii. positioning an x-ray detector adjacent said workpiece to receive x-rays emanating solely from the weld in a plane in which said electron beam lies; and
iv. positioning a collimator between said workpiece and said x-ray dectector for allowing only x-rays emanating from the weld in a direction perpendicular to the direction of said electron beam, to reach said x-ray detector;

said collimator comprising a plurality of spaced parallel plates formed of a material having a high atomic number, each of said plates having a plurality of identical bores there through, the bores of each plate being aligned with the bores of each other plate and with the x-ray detector, to allow only said x-rays emanating in a direction perpendicular to the direction of the electron beam to pass there through to the x-ray detector;

said x-ray detector having an output indicative of the variation, in the direction parallel to the direction of the electron beam, of the intensity of x-rays received by said x-ray detector, thereby to give an indication of the depth of the weld in the workpiece.

Particularly suitable for performing this measuring procedure is an apparatus in which the X-rays, which occur during the welding process and which expand spherically from the location where they develop, are guided through an absorption device, that is a collimator, which is provided between the workpiece and a ray receiver and which consists of several plates which are made from a material of a high atomic number and which are spaced one behind the other, the plates comprising a plurality of bores of equal diameter, which are arranged in their position relative to one another in such a way that the centre lines of corresponding bores, which are on the same level, are exactly in alignment and that the ray receiver, absorption device and workpiece are aligned parallel to one another and are coordinated in height.

Lead plates, which are spaced one behind the other, are suitable as the absorption means. Preferably, each lead plate comprises bores or slots which extend over its entire length at a slight distance from one another. The distance between the centre lines of the bores of the individual lead plates is equal. When the individual lead plates are set up or when the lead plates are installed in a frame, attention has to be paid that the centre lines of corresponding bores, which are vertical to the lead plates in a plane, are exactly in alignment.

An advantageous further development of the mentioned absorption device consists in that the lead plates are arranged at a different distance from one another.

The X-rays which emanate from the piston during welding and which expand in all directions and which are used for measuring the weld seam depth, impinge on the absorption device. During this process, X-rays which do not strike on bores in the first lead plate are absorbed by it. This means that a large proportion of the X-rays, above all those which are incident at an angle which is inclined relative to the centre line of the bore, are absorbed already by the first lead plate.

X-rays which strike the wall of the bore in a manner that is inclined relative to the centre line of the bore of the first lead plate are reflected, following physical laws, on the bore wall and then strike the second lead plate, which absorbs them. The arrangement and number of lead plates ensure that even those X-rays which strike the walls of the bores obliquely several times and which are reflected do not pass through the absorption device, since once on their way they will impinge on a lead plate and be absorbed by it.

Only X-rays which expand in the direction of the centre lines of the bores pass without hindrance through the bores and consequently through the absorption device and impinge on the ray receiver, where they bring about a marking or a signal which indicated, directly or in conjunction with a comparable size, the dimension of the weld seam depth.

The arrangement according to the invention ensures, with a small number of lead plates, that only those X-rays which are suitable for measuring the weld seam depth, namely those which expand through the bores in the direction of the centre lines of the bores, impinge on the ray receiver.

For example, an X-ray film can be used as the ray receiver and be fitted behind the absorption device in such a way that it corresponds in length at least to the length of the absorption plates when these are arranged vertically and the bores in the plates extend exactly horizontally. In such an arrangement, only those X-rays which emerge exactly horizontally from each point of the weld seam and which pass without hindrance through the bores of the absorption plates strike the X-ray film and blacken it. The weld seam depth corresponds exactly to the length of the blackening which extends vertically on the X-ray film. Although the blackening on the X-ray film partially does not completely disappear at the end of the weld seam, it becomes, however, so much weaker there all of a sudden that the end of the weld seam depth is in any case clearly recognisable at this point.

As advantageous further ray receivers there may be used extremely sensitive transmitters, for instance photo elements which have been rendered sensitive to X-rays, which continuously report the depth of penetration of the charge carrier beam to the welding operator. The sensitivity of the transmitters can be selected to be such that these transmitters will only record X-rays having an intensity which exceeds a certain threshold value. In this way, a weak spurious radiation, which might go beyond the actual weld seam depth, can be completely kept away from the read-out.

If there is a requirement for a specific predetermined weld seam depth and if corrections of the welding conditions should become necessary to this end during the welding process, then an automatic control of the welding machine can be brought about by control measures in conjunction with the afore-mentioned transmitter arrangement. By this means, the expenditure required for obtaining workpieces which are welded satisfactorily is very much reduced, which means a considerably lowering of costs.

BRIEF DESCRIPTION OF THE DRAWING

An exemplified embodiment according to the invention will be described in more detail with reference to the drawing which shows an arrangement for carrying out the method.

DESCRIPTION OF THE PREFERRED EMBODIMENT

A piston 3, which is mounted on a movable and rotatable device 4, is treated (machined) by an electron beam 2 emanating from an electron-beam welding tool 1. The piston 3 consists of a piston barrel (body) 5 and an annular (ring) carrier 7 provided with annular grooves 6.

When the electron beam 2 strikes and penetrates the joint 8 of the piston barrel 5 and the annular carrier 7, there develop over the weld seam depth as far as the location 9 X-rays 10 which expand spherically in all directions. These X-rays 10 partly impinge on the absorption device 11, which consists of lead plates 12, which are arranged vertically one behind the other, and an appertaining frame 13. The lead plates 12 comprise bores 14 of equal diameter and are arranged in their position to one another in such a way that the centre lines 15 of corresponding bores, which are on the same level, are in exact alignment. All X-rays which have a different direction of expansion from the direction of the bores 14, which is exactly horizontal here, strike, when passing through the absorption device, points of the lead plates where there are no bores and are absorbed there. Only selected X-rays which have a parallel horizontal direction of expansion 16 strike an X-ray film 17, serving as the ray receiver, and blacken it 18. Since the ray receiver 17, absorption device 11 and piston 3 are aligned in parallel with one another and are co-ordinated in height to one another, the exact respective welding depth T of the electron beam 2 and consequently the depth of the weld seam can be accurately read by referring to these blackenings 18.

We claim:
1. A method for determining the depth of a weld internal of a workpiece during electron beam welding, said method comprising the steps of:
   i. supporting a workpiece in a workpiece support;
   ii. directing an electron beam into said workpiece for effecting a weld within the workpiece;
   iii. positioning an x-ray detector adjacent said workpiece to receive x-rays emanating solely from the weld in a plane in which said electron beam lies; and
   iv. postioning a collimator between said workpiece and said x-ray detector for allowing only x-rays emanating from the weld in a direction perpendicular to the direction of said electron beam, to reach said x-ray detector;
   said collimator means comprising a plurality of spaced parallel plates formed of a material having a high atomic number, each of said plates having a plurality of identical bores therethrough, the bores of each plate being aligned with the bores of each other plate and with the x-ray detector, to allow only said x-rays emanating in a direction perpendicular to the direction of the electron beam to pass there through to the x-ray detector,
   said x-ray detector having an output indictive of the variation, in the direction parallel to the direction of the electron beam, of the intensity of x-rays received by said x-ray detector, thereby to give an indication of the depth of the weld in the workpiece.
2. A method according to claim 1 wherein said plates are not equally spaced one from another.

* * * * *